US012064491B2

(12) United States Patent
Maina-Nock et al.

(10) Patent No.: US 12,064,491 B2
(45) Date of Patent: *Aug. 20, 2024

(54) RADIOLABELED GRPR-ANTAGONISTS FOR DIAGNOSTIC IMAGING AND TREATMENT OF GRPR-POSITIVE CANCER

(71) Applicant: Advanced Accelerator Applications International SA, Geneva (CH)

(72) Inventors: Theodosia Maina-Nock, Athens (GR); Berthold Artur Nock, Athens (GR); Marion de Jong Hendriks, Vlaardingen (NL)

(73) Assignee: Advanced Accelerator Applications International SA, Geneva (CH)

( * ) Notice: Subject to any disclaimer, the term of this patent is extended or adjusted under 35 U.S.C. 154(b) by 317 days.

This patent is subject to a terminal disclaimer.

(21) Appl. No.: 17/383,577

(22) Filed: Jul. 23, 2021

(65) Prior Publication Data

US 2021/0346529 A1     Nov. 11, 2021

Related U.S. Application Data

(63) Continuation of application No. 16/580,990, filed on Sep. 24, 2019, now Pat. No. 11,083,805, which is a continuation of application No. 15/817,776, filed on Nov. 20, 2017, now abandoned, which is a continuation of application No. 14/431,096, filed as application No. PCT/US2013/061712 on Sep. 25, 2013, now Pat. No. 9,839,703.

(60) Provisional application No. 61/705,513, filed on Sep. 25, 2012.

(51) Int. Cl.
   *A61K 51/08*        (2006.01)
   *C07B 59/00*        (2006.01)

(52) U.S. Cl.
   CPC .......... *A61K 51/088* (2013.01); *A61K 51/08* (2013.01); *C07B 59/008* (2013.01)

(58) Field of Classification Search
CPC ...... A61K 51/00; A61K 51/08; A61K 51/088; C07B 59/008; C07B 59/00; A61P 1/00; A61P 1/04; A61P 1/18; A61P 11/00; A61P 13/08; A61P 13/12; A61P 15/00; A61P 17/00; A61P 25/00; A61P 35/00; A61P 35/04; A61P 43/00
USPC ........ 424/1.11, 1.65, 1.69, 9.1, 9.2, 9.3, 9.4, 424/9.5; 534/7, 10–16; 514/1, 1.1, 19.2, 514/19.3, 19.4, 19.5, 19.6, 21.7; 530/300, 530/329
See application file for complete search history.

(56) References Cited

U.S. PATENT DOCUMENTS

| 4,943,561 | A | 7/1990 | Heimbrook et al. |
| 5,019,647 | A | 5/1991 | Riemen et al. |
| 5,028,692 | A | 7/1991 | Oliff et al. |
| 5,620,955 | A | 4/1997 | Knight et al. |
| 6,545,125 | B1 | 4/2003 | Fujii |
| 9,839,703 | B2 * | 12/2017 | Maina-Nock ........... A61P 11/00 |
| 10,449,260 | B2 | 10/2019 | Maina-Nock et al. |
| 11,083,805 | B2 * | 8/2021 | Maina-Nock ............. A61P 1/18 |
| 2007/0269375 | A1 | 11/2007 | Chen et al. |
| 2011/0097266 | A1 | 4/2011 | Maecke et al. |

FOREIGN PATENT DOCUMENTS

| CA | 2045494 A1 | 5/1991 |
| JP | H02-250898 A | 10/1990 |
| JP | H04-502629 A | 5/1992 |
| JP | 2006-528644 A | 12/2006 |
| WO | 93/16105 A1 | 8/1993 |
| WO | 99/25729 A1 | 5/1999 |
| WO | 2009/109332 A1 | 9/2009 |
| WO | 2012/069410 A1 | 5/2012 |
| WO | 2014/052471 A1 | 4/2014 |

OTHER PUBLICATIONS

Yang et al., "F-Labeled GRPR Agonists and Antagonists: A Comparative Study in Prostate Cancer Imaging," Theranostics, 1: 220-229 (2011).
Darker et al., "Discovery of Potent and Selective Peptide Agonists at the GRP-preferring Bombesin Receptor (BB2)," Journal of Peptide Science, 7: 598-605 (2001).
Gill et al., "A modular platform for the rapid site-specific radiolabeling of proteins with 18F exemplified by quantitative positron emission tomography of human epidermal growth factor receptor 2," Journal of Medicinal Chemistry, 52(19): 5820 (2009).
Jakubke et al., "Aminoacids, Peptides, Proteins," M: Mir, pp. 92-94 (1985).
Abd-Elgaliel et al., "Design, Synthesis, and Biological Evaluation of an Antagonist-Bombesin Analogue as Targeting Vector", Bioconjugate Chemistry, Oct. 1, 2008, pp. 2040-2048, vol. 19 No. 10.
Abiraj et al., "Tetraamine-Derived Bifunctional Chelators for Technetium-99m Labelling: Synthesis, Bioconjugation and Evaluation as Targeted SPECT Imaging Probes for GRP-Receptor-Positive Tumours", Chemistry A European Journal, Feb. 15, 2010, pp. 2115-2124, vol. 16, Issue 7, Available online Jan. 11, 2010.

(Continued)

*Primary Examiner* — D. L. Jones
(74) *Attorney, Agent, or Firm* — Morgan, Lewis & Bockius LLP

(57) ABSTRACT

The present invention relates to probes for use in the detection, imaging, diagnosis, targeting, treatment, etc. of cancers expressing the gastrin releasing peptide receptor (GRPR). For example, such probes may be molecules conjugated to detectable labels which are preferably moieties suitable for detection by gamma imaging and SPECT or by positron emission tomography (PET) or magnetic resonance imaging (MRI) or fluorescence spectroscopy or optical imaging methods.

9 Claims, 8 Drawing Sheets

Specification includes a Sequence Listing.

(56) References Cited

OTHER PUBLICATIONS

Blauenstein et al., "Chemical and Biological Properties of a Cationic Tc-Tetraamine Complex", Int. J. Appl. Radial. Isol., 1985, pp. 315-317, vol. 36, No. 4.
Bunnett et al., "Metabolism and Inactivation of Gastrin Releasing Peptide by Endopeptidase-24.11 ", Quarterly Journal of Experimental Physiology, 1989, pp. 727-734, vol. 74.
Burke et al., "Novel Immunoconjugates Comprised of Streptonigrin and 17-amino-geldanamycin Attached via a :lipeptide-p-aminobenzyl-amine Linker System", Bioorganic and Medicinal Chemistry Letters, May 15, 2009, pp. J650-2653, vol. 19.
Heimbrook et al., "Gastrin Releasing Peptide Antagonists with Improved Potency and Stability", Journal of Medicinal Chemistry, Jul. 1, 1991, pp. 2102-2107, vol. 34 No. 7.
Hoffman et al., "Novel Series of 111 In-Labeled Bombesin Analogs as Potential Radiopharmaceuticals for Specific Targeting of Gastrin-Releasing Peptide Receptors Expressed on Human Prostate Cancer Cells", Journal of Nuclear Medicine, May 1, 2003, pp. 823-831, vol. 44, No. 5.
Liu, "The role of coordination chemistry in the development of target-specific radiopharmaceuticals", The Royal Society of Chemistry, 2004, pp. 445-461, vol. 33.
Maina et al., "Species Differences of Bombesin Analog Interactions with GRP-R Define the Choice of Animal Models in the Development of GRP-R-Targeting Drugs", J Nucl Med, 2005, pp. 823-830, vol. 46.
Mansi et al., "Evaluation of a 1,4,7, 10-Tetraazacyclododecane-1,4,7, 10-Tetraacetic Acid-Conjugated Bombesin-Based Radioantagonist for the Labeling with Single-Photon Emission Computed Tomography, Positron Emission Tomography, and Therapeutic Radionuclides" Clinical Cancer Research, Aug. 11, 2009, pp. 5240-5249, vol. 15, No. 16.
Nock et al., "[99mTc]Demobesin 1, a Novel Potent Bombesin Analogue for GRP Receptor-Targeted Tumour maging", European Journal of Nuclear Medicine and Molecular Imaging, Feb. 1, 2003, pp. 247-258, vol. 30 No. 2.
Parry et al., "In Vitro and in Vivo Evaluation of 64Cu-Labeled DOTA-Linker-Bombesin (7-14)", Bioconjug Chem, J007, pp. 1110-1117, vol. 18, No. 4.
Rogers et al., "Localization of Iodine, 125-mIP-Des-Met<14>-Bombesin (7-13) NH2 in Ovarian Carcinoma InducedExpress the Gastrin Releasing Peptide Receptor by Adenoviral Vector-Mediated Gene Transfer", Journal of Nuclear Medicine, 1997, pp. 1221-1229, vol. 38 No. 8.
Safavy et al., "Synthesis of Bombesin Analogs for Radiolabeling with Rhenium-188", Cancer, Jan. 1, 1997, pp. J354-J2359, vol. 80 No. 12.
Shipp et al., "CD10/neutral endopeptidase 24.11 hydrolyzes bombesin-like peptides and regulates the growth of , mall cell carcinomas of the lung", Proc. Natl. Acad. Sci. USA, 1991, pp. 10662-10666, vol. 88.
Wael et al., "Design, Synthesis and Biological Evaluation of a Radiolabelled Antagonist-Bombesin Analog as Targeting Vector", Bioconjug Chem, 2008, pp. 2040-2048, vol. 19, No. 10.
Koroliuk, "Radiation diagnosis," Textbook, 3rd edition (2015). Title sheet and pp. 103-104 in a foreign language and title sheet and pp. 103-104 translated in English.

* cited by examiner

```
                       SEQUENCE LISTING

<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: /note="DPhe"

<400> SEQUENCE: 1

Phe Gln Trp Ala Val Gly His
1               5

<210> SEQ ID NO 2
<211> LENGTH: 7
<212> TYPE: PRT
<213> ORGANISM: Artificial Sequence
<220> FEATURE:
<223> OTHER INFORMATION: Sythetic
<220> FEATURE:
<221> NAME/KEY: MISC_FEATURE
<222> LOCATION: (1)..(1)
<223> OTHER INFORMATION: /note="DPhe"

<400> SEQUENCE: 2

Phe Gln Trp Ala Val Gly His
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: /note="DPhe"

<400> SEQUENCE: 3

Phe Gln Trp Ala Val Gly His
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: /note="DTyr"

<400> SEQUENCE: 4

Thr Gln Trp Ala Val Gly His
1               5

<210> SEQ ID NO 5
<211> LENGTH: 7
<212> TYPE: PRT
```

```
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: /replace=" " or "Asn" or "Thr" or "Thi" or
      "Cpa" or "alpha-Nal" or "beta-Nal" or "Tpi" or "Tyr" or "o-I-Tyr"
      or "Trp" or "5-F-Phe"
<220> FEATURE:
<221> NAME/KEY: MISC_FEATURE
<222> LOCATION: (1)..(7)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (2)..(2)
<223> OTHER INFORMATION: /replace="Asn" or "His"
<220> FEATURE:
<221> NAME/KEY: VARIANT
<222> LOCATION: (3)..(3)
<223> OTHER INFORMATION: /replace="Tpi"
<220> FEATURE:
<221> NAME/KEY: VARIANT
<222> LOCATION: (4)..(4)
<223> OTHER INFORMATION: /replace="Ser" or "Val"
<220> FEATURE:
<221> NAME/KEY: VARIANT
<222> LOCATION: (5)..(5)
<223> OTHER INFORMATION: /replace="Ser" or "Thr"
<220> FEATURE:
<221> NAME/KEY: VARIANT
<222> LOCATION: (6)..(6)
<223> OTHER INFORMATION: /replace="Sar" or "D-Ala" or "beta-Ala"
<220> FEATURE:
<221> NAME/KEY: VARIANT
<222> LOCATION: (7)..(7)
<223> OTHER INFORMATION: /replace="(3-Me)His"

<400> SEQUENCE: 5

Phe Gln Trp Ala Val Gly His
1               5
```

RADIOLABELED GRPR-ANTAGONISTS FOR DIAGNOSTIC IMAGING AND TREATMENT OF GRPR-POSITIVE CANCER

INCORPORATION OF SEQUENCE LISTING

The content of the electronically submitted sequence listing the ASCII text file (Name: GRPR_SubstituteSequenceListing_ST25.txt; Size: 2439 bytes; and Date of Creation: Sep. 19, 2019) filed with the application is incorporated herein by reference in its entirety.

BACKGROUND OF THE INVENTION

Cancer cells have been shown to express a variety of specific biomolecules such as peptide-receptors, which may serve as recognition sites for a wide range of circulating vectors, as for example peptide-ligands. In case the expression of the target-receptor is higher on malignant cells than in surrounding healthy tissue, the opportunity arises to exploit the interaction between these two molecular entities. For diagnostic imaging or targeted therapy applications, a natural peptide-ligand could be modified to stably bind a diagnostic or a therapeutic radionuclide, e.g. a radiometal or a radiohalogen.

In many cases, a bifunctional chelator is covalently coupled via a carboxyl-functionality to the N-terminal amine of the peptide-ligand to form a peptide bond. In order to increase the biological stability, hydrophilicity, receptor binding affinity and/or internalization efficacy, further modifications of native receptor ligands are attempted, such as strategic amino acid replacements in the peptide chain. Alternatively, introduction of suitable spacers between the chelator and the peptide receptor recognition site or hetero/homo peptide-multimerization may equally lead to advantageous improvements of many biological parameters eventually improving overall pharmacokinetics and target accumulation of the radioactive probe.

The resulting peptide-chelate conjugate after labeling with a diagnostic or a therapeutic radionuclide (radiopeptide) is administered to the patient. The radiopeptide selectively accumulates on cancer-site(s) through specific interaction with the target-molecule, i.e. its cognate peptide-receptor, highly expressed on the tumor. In case of a diagnostic radionuclide, the tumor and metastases are then localized by imaging the site(s) where the radioactive decay occurs using an external imaging device. When the peptide-chelate conjugate is labeled with a therapeutic radionuclide, a radiotoxic load is delivered specifically to the primary tumor and its metastases. The therapeutic radionuclide will then decay on the cancer site(s), releasing corpuscular energy to kill or to reduce (the growth of) the lesions.

This strategy has been elegantly exploited in the area of somatostatin and its receptors. The latter are abundantly expressed in a variety of human tumors, and especially in neuroendocrine tumors (NETs). The advent of OctreoScan® ([$^{111}$In-DTPA]octreotide) in clinical practice for the successful diagnostic imaging of NETs was soon followed by many new improved somatostatin analogs labeled with a wide range of medically relevant radiometals useful not only for conventional imaging with a gamma-camera, but also for PET and, most importantly, for radionuclide therapy. Ongoing clinical trials have revealed the therapeutic efficacy of these new radiopeptides.

Peptide-receptors and their ligands have emerged as attractive molecular tools in cancer diagnosis and therapy. For example, high density expression of gastrin releasing peptide receptors (GRPRs) has been documented in several frequently occurring human tumors, such as in prostate cancer, mammary carcinoma and lung cancer. As a consequence, GRPRs have lately been gaining momentum as preferred molecular targets for radiolabeled bombesin-like peptides with the aim to upgrade the diagnostic and therapeutic arsenal of nuclear oncology.

Bombesin (BBN) is a tetradecapeptide initially isolated from the skin of the European frog *Bombina bombina*. Bombesin and its related peptides affect thermoregulation and food-intake after binding to specific receptors in humans. These receptors comprise three subtypes in mammals, the neuromedin B receptor (NMBR or $BB_1R$) with a high affinity for NMB, the GRPR (or $BB_2R$) with a high affinity for GRP and the $BB_3R$, which is an orphan receptor with no-known ligand identified yet. Amphibian BBN binds to NMBR and GRPR subtypes with a high affinity. NMB and GRP are the mammalian counterparts of amphibian BBN and are all related in structure.

Most radiolabeled BBN-like peptides developed for molecular imaging and radionuclide therapy of human tumors have been based on native BBN, or on its C-terminal octapeptide fragment still able to bind the GRPR. These analogs modified as detailed above typically exhibit agonistic properties and internalize in the intracellular region of malignant cells after binding to the GRPR. This property translates into a high accumulation of the radiolabel in the $GRPR^+$ lesions, thereby enhancing either diagnostic sensitivity or therapeutic efficacy.

Unfortunately, BBN-like peptides are potent GRPR-agonists, eliciting adverse effects related to gastrointestinal motility and thermoregulation when intravenously (iv) administered in human even in small amounts. In addition, BBN-like peptides are mitogenic. The above properties have restrained the thorough clinical validation and/or the eventual commercial exploitation of a few promising agonist-based radiolabeled bombesins. This is particularly relevant in the case of targeted radionuclide therapy whereby higher peptide amounts need to be iv administered in patients.

Unlike radiolabeled BBN agonists, radiolabeled somatostatin-agonists, which internalize equally well into somatostatin receptor-expressing malignant cells, do not elicit undesirable physiological effects after iv injection in humans. This fact has fostered the extended and systematic clinical validation of a few promising radiolabeled somatostatins even in the domain of radionuclide tumor therapy.

The radiotracer ([$^{99m}$Tc]Demobesin 1, [$^{99m}$Tc—$N_4$'] DPhe-Gln-Trp-Ala-Val-Gly-His-Leu-NHEt) is known and used in mice bearing human prostate cancer PC-3 xenografts, where [$^{99m}$Tc]Demobesin 1 showed exceptionally superior pharmacokinetic properties as opposed to similarly affine bombesin-based agonists, as for example [$^{99m}$Tc] Demobesin 3-6. Besides its significantly higher tumor accumulation, [$^{99m}$Tc]Demobesin 1 cleared very rapidly from the body of mice and the pancreas, a strongly GRPR-positive organ.

Although first studies in a limited number of prostate cancer patients verified the excellent tolerability of the radiotracer, they revealed a sub-optimal pharmacokinetic profile in humans preventing a further expanded clinical application as a diagnostic imaging tool. More specifically, [$^{99m}$Tc]Demobesin 1 despite its rapid body and pancreas clearance and its rather good in vivo stability, exhibited insufficient retention in malignant lesions in humans as compared to radiolabeled BBN-like agonists. Furthermore, [$^{99m}$Tc]Demobesin 1 was designed for diagnostic imaging using conventional gamma camera or SPECT and is unsuitable for PET or radionuclide therapy applications. Although labeling with the PET radionuclide $^{94m}$Tc is feasible by means of the acyclic $N_4$-system, the medical use of this radionuclide is restricted both by sub-optimal nuclear characteristics and inconvenient production. On the other hand, therapeutic options are restricted to $^{186/188}$Re, as the $N_4$-chelator cannot stably bind most of bi- and trivalent radiometals used in nuclear medicine.

It is therefore the object of the present invention to achieve high uptake and retention of a diagnostic and a therapeutic radiolabel selectively to GRPR$^+$-cancer, both primary and metastatic.

SUMMARY OF THE INVENTION

The present invention relates to probes for use in the detection, imaging, diagnosis, targeting, treatment, etc. of cancers expressing the gastrin releasing peptide receptor (GRPR). Such probes may be molecules conjugated to detectable labels which are preferably moieties suitable for detection by gamma imaging and SPECT or by positron emission tomography (PET) or magnetic resonance imaging (MRI) or fluorescence spectroscopy or optical imaging methods. Such probes may also be molecules conjugated to anticancer drugs or to moieties containing a therapeutic radionuclide and are able to deliver a cytotoxic load such as a cytotoxic drug or a therapeutic radionuclide at the site(s) of disease.

Certain embodiments of the invention are drawn to a GRPR-antagonist of the general formula:

MC-S-P wherein:
at least one (radio)metal (M) and a chelator (C) which stably binds M; alternatively MC may represent a Tyr- or a prosthetic group carrying a (radio)halogen;
S is an optional spacer covalently linked between the N-terminal of P and C and may be selected to provide a means for (radio) halogenation;
P is a GRP receptor peptide antagonist of the general formula:

Xaa$_1$-Xaa$_2$-Xaa$_3$-Xaa$_4$-Xaa$_5$-Xaa$_6$-Xaa$_7$-Z

Xaa$_1$ is not present or is selected from the group consisting of amino acid residues Asn, Thr, Phe, 3-(2-thienyl)alanine (Thi), 4-chlorophenylalanine (Cpa), α-naphthylalanine (α-Nal), β-naphthylalanine (β-Nal), 1,2,3,4-tetrahydronorharman-3-carboxylic acid (Tpi), Tyr, 3-iodo-tyrosine (o-I-Tyr), Trp, pentafluorophenylalanine (5-F-Phe) (all as L- or D-isomers);
Xaa$_2$ is Gln, Asn, His
Xaa$_3$ is Trp, 1,2,3,4-tetrahydronorharman-3-carboxylic acid (Tpi)
Xaa$_4$ is Ala, Ser, Val
Xaa$_5$ is Val, Ser, Thr
Xaa$_6$ is Gly, sarcosine (Sar), D-Ala, β-Ala
Xaa$_7$ is His, (3-methyl)histidine (3-Me)His
Z is selected from —NHOH, —NHNH$_2$, —NH-alkyl, —N(alkyl)$_2$, or —O-alkyl
or

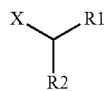

wherein X is NH (amide) or O (ester) and R1 and R2 are the same or different and selected from a proton, a (substituted)alkyl, a (substituted) alkyl ether, an aryl, an aryl ether or an alkyl-, halogen, hydroxyl or hydroxyalkyl substituted aromatic group.

In certain embodiments the GRPR-antagonist of the invention is as described above and wherein Z is preferably selected from one of the following formulae, wherein X is NH or O:

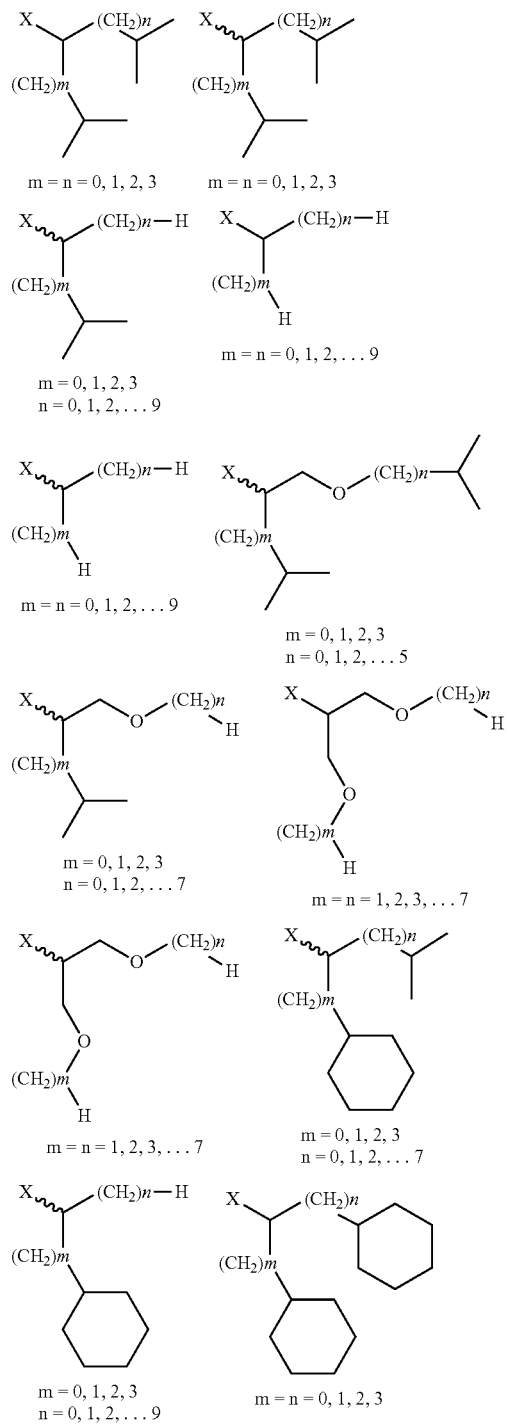

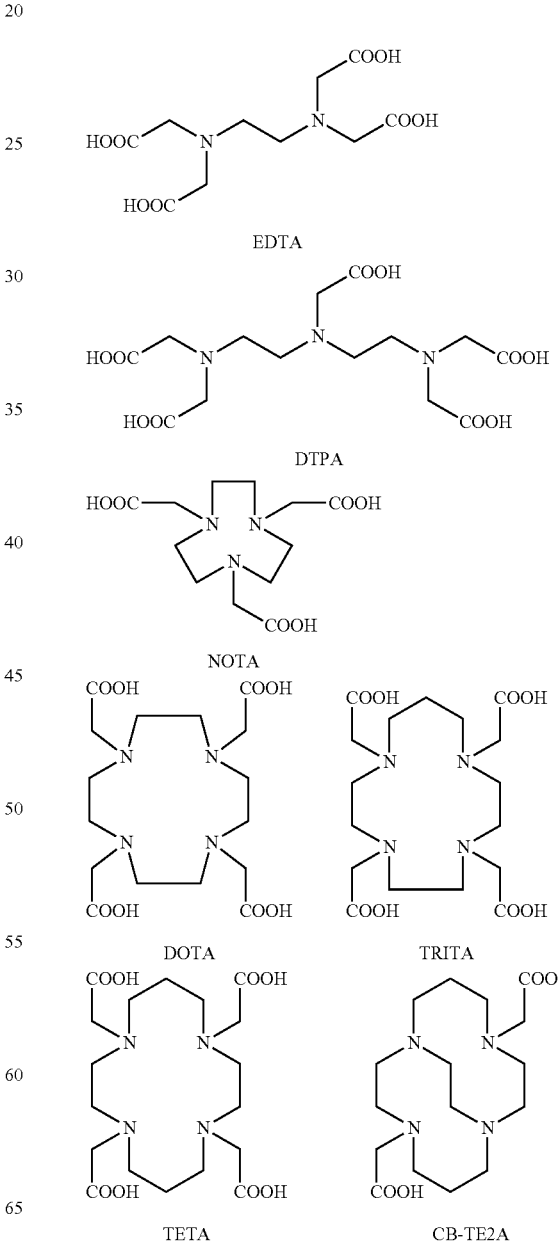

-continued

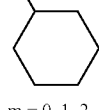

m = 0, 1, 2, 3
n = 0, 1, 2, ... 9

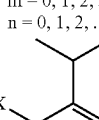

m = n = 0, 1, 2, 3

m = 0, 1, 2, 3
n = 0, 1, 2, ... 9

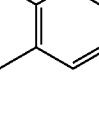

R = H, Cl, Br, I
m = 0, 1, 2, 3
n = 0, 1, 2, ... 9

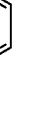

Hal = Cl, Br, I
m = 0, 1, 2, 3
n = 0, 1, 2, ... 9

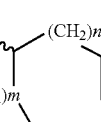

n = 1, 2, 3, ... 10

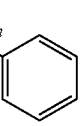

Further, in certain embodiments, the GRPR-antagonist is as described above and R1 is the same as R2.

In certain of any of the embodiments described above, the invention is drawn to wherein P is selected from the group consisting of:

```
                                            (SEQ ID NO: 1)
DPhe-Gln-Trp-Ala-Val-Gly-His- NH-CH[CH2-CH(CH3)2]2;

(SEQ ID NO: 2)
DPhe-Gln-Trp-Ala-Val-Gly-His- O-CH[CH2-CH(CH3)2]2;

(SEQ ID NO: 3)
DPhe-Gln-Trp-Ala-Val-Gly-His-
NH-CH(CH2-CH2-CH2-CH3)2;

(SEQ ID NO: 4)
DTyr-Gln-Trp-Ala-Val-Gly-His- NH-CH[CH2-CH(CH3)2]2.
```

In certain of any of the embodiments described above, the invention is drawn to wherein the radionuclide metal M or radiohalogen is suitable for diagnostic or therapeutic use, in particular for imaging or radionuclide therapy and selected from the group consisting of: $^{111}$In, $^{133m}$In, $^{99m}$Tc, $^{94m}$Tc, $^{67}$Ga, $^{66}$Ga, $^{68}$Ga, $^{52}$Fe, $^{69}$Er, $^{72}$As, 97Ru, $^{203}$Pb, $^{62}$Cu, $^{64}$Cu, $^{67}$Cu, $^{186}$Re, $^{188}$Re, $^{86}$Y, $^{90}$Y, $^{51}$Cr, $^{52m}$Mn, $^{157}$Gd, $^{177}$Lu, $^{161}$Tb, $^{169}$Yb, $^{175}$Yb, $^{105}$Rh, $^{166}$Dy, $^{166}$Ho, $^{153}$Sm, $^{149}$Pm, $^{151}$PM, $^{172}$Tm, $^{121}$Sn, $^{177m}$Sn, $^{213}$Bi, $^{142}$Pr, $^{143}$Pr, $^{198}$Au, $^{199}$Au, halogens: $^{123}$I, $^{124}$I, $^{125}$I, $^{18}$F, a.o.

In certain of any of the embodiments described above, the invention is drawn to wherein the metal chelator C is a metal chelator for di- and trivalent metals.

In certain of any of the embodiments described above, the invention is drawn to wherein the metal chelator for di- and trivalent metals is a DTPA-, NOTA-, DOTA-, or TETA-based chelator or a mono- or bifunctional derivative thereof.

In certain of any of the embodiments described above, the invention is drawn to wherein the metal chelator C is selected from the group consisting of:

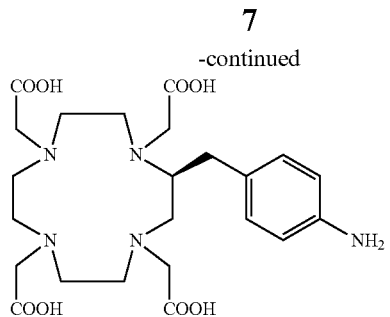

bifunctional DOTA

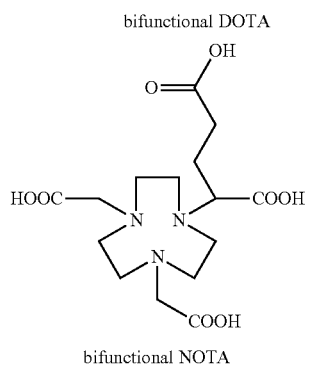

bifunctional NOTA

In certain of any of the embodiments described above, the invention is drawn to wherein the metal chelator C is a metal chelator for technetium or rhenium.

In certain of any of the embodiments described above, the invention is drawn to wherein C is selected from acyclic tetraamine-, cyclam-, PnAO-, or tetradentate chelators containing $P_2S_2$-, $N_2S_2$- and $N_3S$-donor atom sets and mono- and bifunctional derivatives thereof, or HYNIC/co-ligand-based chelators, or bi- and tridentate chelators forming organometallic complexes via the tricarbonyl technology.

In certain of any of the embodiments described above, the invention is drawn to wherein C is selected from the group consisting of:

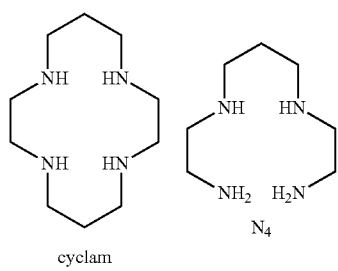

cyclam     $N_4$

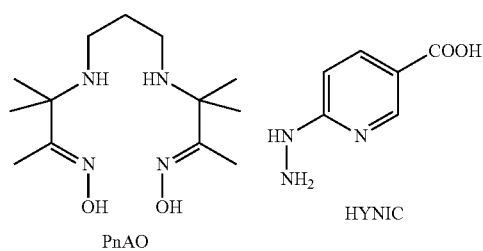

PnAO     HYNIC

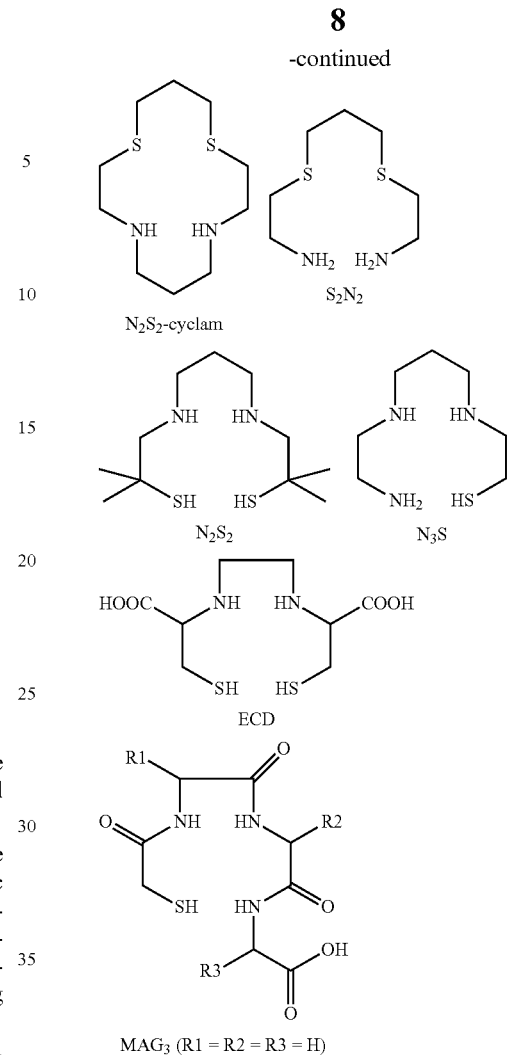

$N_2S_2$-cyclam     $S_2N_2$ $N_2S_2$     $N_3S$

ECD $MAG_3$ (R1 = R2 = R3 = H)

-Xaa-Cys-Xaa-Cys-Xaa-

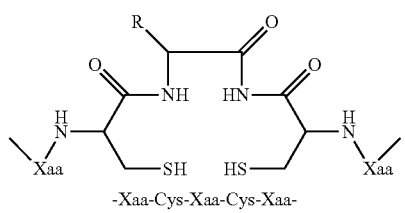

$P_2S_2$

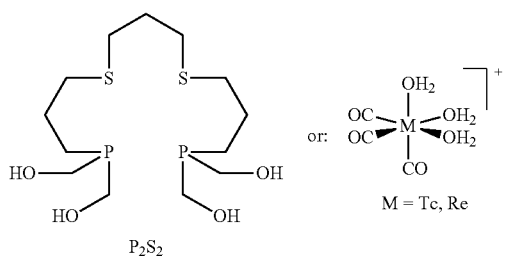

M = Tc, Re

In certain of any of the embodiments described above, the invention is drawn to wherein the spacer S is linked between P and C by covalent bonds and may be selected to provide a means for (radio)iodination.

In certain of any of the embodiments described above, the invention is drawn to wherein S is selected from the group consisting of:

a) aryl containing residues of the formulae:

[Structure: PABA - p-aminobenzoic acid]

[Structure: PABZA - p-aminobenzylamine]

[Structure: PDA - phenylenediamine]

[Structure: PAMBZA - p-(aminomethyl)benzylamine]

wherein PABA is p-aminobenzoic acid, PABZA is p-aminobenzylamine, PDA is phenylenediamine and PAMBZA is p-(aminomethyl)benzylamine;

b) dicarboxylic acids, ω-aminocarboxylic acids, α,ω-diaminocarboxylic acids or diamines of the formulae:

[Structures showing:
HOOC-(CH$_2$)$_n$-COOH, n = 0, 1, 2, ...
DIG (diglycolic acid)
IDA (iminodiacetic acid)
H$_2$N-(CH$_2$)$_n$-COOH, n = 0, 1, 2, ...
H$_2$N-CH(NH$_2$)-(CH$_2$)$_n$-COOH, n = 0, 1, 2, ...
H$_2$N-(CH$_2$)$_n$-NH$_2$, n = 0, 1, 2, ...]

wherein DIG is diglycolic acid and IDA is iminodiacetic acid;

c) PEG spacers of various chain lengths, in particular PEG spacers selected from the formulae:

[Structure: PEG-1]

[Structure: PEG-2]

[Structure: PEG-3]

[Structure: PEG-4]

[Structure: H$_2$N-[CH$_2$CH$_2$O]$_n$-[CH$_2$]$_m$-C(O)OH
n = 1, 2, 3, ... until 36
m = 0, 1, 2, 3, 4, 5]

c) α- and β-amino acids, single or in homologous chains of various chain lengths or heterologous chains of various chain lengths, in particular:

[Structure: Xaa]   [Structure: βXaa]

GRP(1-18), GRP(14-18), GRP(13-18), BBN(1-5), or [Tyr$^4$]BBN(1-5); or d) combinations of a, b and c.

In certain of any of the embodiments described above, the invention is drawn a GRPR-antagonist selected from the group consisting of compounds of the formulae:

[Structure with PABZA and DIG linker]
PABZA: p-Aminobenzylamine
DIG: Diglycolic Acid

[Structure with Gly and PABA linker]
PABA: p-Aminobenzoic acid

-continued

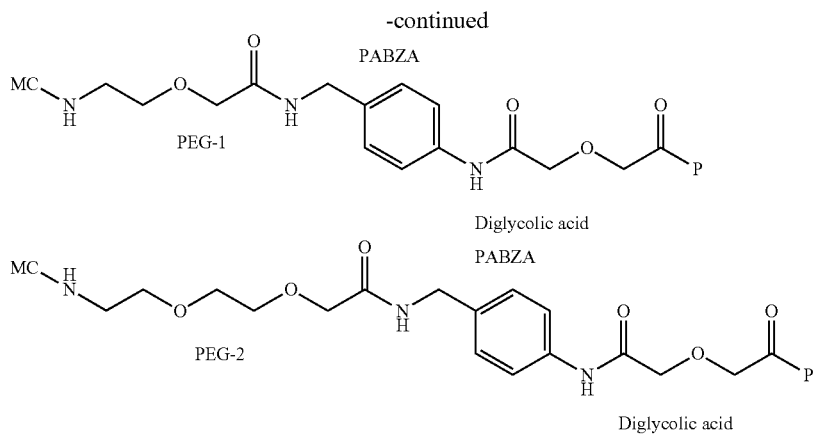

wherein MC and P are as defined in any one of the preceding.

In certain embodiments of the invention is drawn to a GRPR-antagonist as described in any of the above embodiments for use as a medicament.

In certain embodiments of the invention is drawn to a GRPR-antagonist as described in any of the above embodiments for use as diagnostic or therapeutic agent for detecting, diagnosing or treating primary and/or metastatic GRPR$^+$ cancer.

In certain embodiments of the invention is drawn to a GRPR-antagonist as described in any of the above embodiments, wherein the cancer is selected from prostate cancer, breast cancer, small cell lung cancer, colon carcinoma, gastrointestinal stromal tumors, gastrinoma, renal cell carcinomas, gastroenteropancreatic neuroendocrine tumors, oesophageal squamous cell tumors, neuroblastomas, head and neck squamous cell carcinomas, as well as in ovarian, endometrial and pancreatic tumors displaying neoplasia-related vasculature that is GRPR$^+$.

In certain embodiments of the invention is drawn to a GRPR-antagonist as described in any of the above embodiments, wherein the cancer is a human cancer.

Certain embodiments of the invention are drawn to a therapeutic composition, comprising a GRPR-antagonist as described in any of the embodiments above and a therapeutically acceptable excipient.

DETAILED DESCRIPTION

Figure 1A:
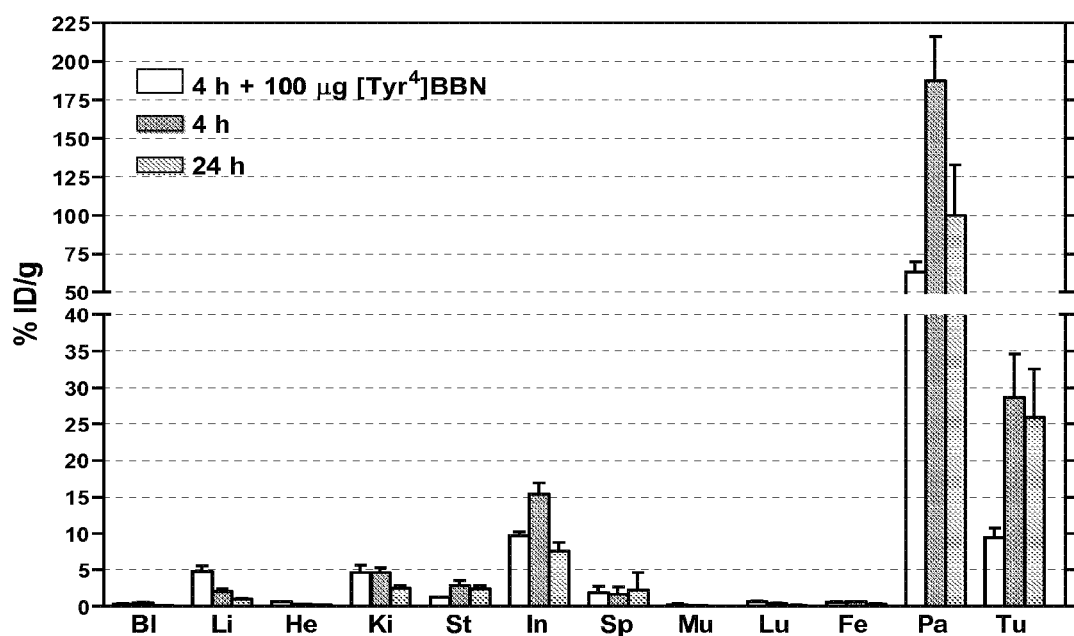
FIG. 1A. Shows the biodistribution of [$^{111}$In]NeoBOMB-1 ($^{111}$In-DOTA-(p-aminobenzylamine-diglycolic acid)-[D-Phe$^6$,His-NHCH[(CH$_2$CH(CH$_3$)$_2$]$_2$$^{12}$,des-Leu$^{13}$,des-Met$^{14}$]BBN(6-14)) in female SCID mice bearing PC-3 tumors (hGRPR$^+$).

The research leading to the invention has unexpectedly revealed an alternative route for effective in vivo targeting of somatostatin-positive tumors, namely the use of somatostatin receptor antagonists. Most surprisingly and against their inability to internalize, such analogs have shown a much higher uptake and retention in animal xenografts and a very rapid washout from background tissues.

A tentative explanation for the higher tumor uptake of somatostatin receptor antagonists is their ability to bind to a significantly higher number of the overall somatostatin receptor population available on the cell-membrane of cancer cells than their internalizing agonistic counterparts.

According to the invention, GRPR-antagonists are chemically modified to accommodate a diagnostic and/or therapeutic radionuclide that they stably bind. After administration in a human or an animal subject they serve as a molecular vehicle to transfer a radiodiagnostic signal and/or a radiotoxic load on the primary GRPR$^+$-tumor and its metastases.

More specifically, it was found according to the invention that administration of certain novel GRPR-antagonist-based radioligands unexpectedly resulted in an unprecedentedly high and specific uptake and a remarkably prolonged retention of human GRPR$^+$-xenografts in mice in contrast to [$^{99m}$Tc]Demobesin 1. Furthermore, these agents showed significantly higher metabolic stability after injection in mice, compared to [$^{99m}$Tc]Demobesin 1.

The GRPR-antagonists of the invention have important structural differences in relation to the original [$^{99m}$Tc]Demobesin 1 motif. Firstly, their labeling with a wide range of bi- and trivalent radiometals, but also with $^{99m}$Tc and $^{186/188}$Re, is made possible by coupling of suitable bifunctional chelators at their N-terminus in addition to tetraamine-related frameworks. In this way, radiodiagnostic imaging is possible with SPECT and PET with gamma and positron-emitters while labeling with beta-, Auger and alpha emitters is feasible as well, opening the opportunity for therapeutic applications. Then, their metabolic stability and pharmacokinetic profile, especially in terms of tumor-retention has largely improved, as demonstrated by preclinical biodistribution results in female SCID mice bearing human PC-3 xenografts presented at length.

More specifically, the structure of new analogs comprises the following parts:

a) The chelator attached to the N-terminus—this can be either an acyclic or a cyclic tetraamine, HYNIC, $N_3S$- chelators and derivatives thereof, linear or cyclic polyamines and polyaminopolycarboxylates like DTPA, EDTA, DOTA, NOTA, NOTAGA, TETA and their derivatives, a.o. In addition, a suitable group, such a prosthetic group or a Tyr, for labeling with radiohalogens, can be introduced at this position;

b) The radionuclide—this may be i) a gamma emitter, such as $^{99m}Tc$, $^{111}In$, $^{67}Ga$, $^{131}I$, $^{125}I$, a.o., suitable for imaging with a conventional gamma-camera, a SPECT or an hybrid SPECT/CT or SPECT/MRI system; ii) a positron emitter, such as $^{68}Ga$, $^{66}Ga$, 64Cu, $^{86}Y$, $^{44}Sc$, $^{124}I$, $^{18}F$, a.o., suitable for imaging with a PET or a hybrid PET/CT or PET/MRI system, or iii) a beta, Auger or alpha emitter, such as $^{186}Re$, $^{188}Re$, $^{90}Y$, $^{177}Lu$, $^{111}In$, $^{67}Cu$, $^{212}Bi$, $^{175}Yb$, $^{47}Sc$, $^{131}I$, $^{125}I$, etc., suitable for radionuclide therapy;

c) The spacer between the chelator and the peptide motif, which may vary in length, type and lipophilicity and may include PEGx (x=0-20), natural and unnatural amino acids, sugars, alkylamino residues or combinations thereof;

d) The peptide chain, with strategic amino acid replacements undertaken with D-amino acids, unnatural amino acids and other suitable residues.

e) The C-terminus, wherein the both $Le^{13}$ and $Met^{14}$-$NH_2$ in the native BBN sequence have been omitted. Terminal $His^{12}$ is present as the amidated or ester form, whereby amides or esters may be represented by several mono- and di-alkylamides, aromatic amides or mixed alkyl-aryl amides, or alkyl and/or aryl esters.

The invention thus relates to GRPR-antagonists of the general formula

MC-S-P wherein:

MC is a metal chelate, which comprises:
at least one (radio)metal (M) and a chelator (C) which stably binds M; alternatively MC may represent a Tyr- or a prosthetic group carrying a (radio)halogen.

S is an optional spacer covalently linked between the N-terminal of P and C and may be selected to provide a means for (radio) halogenation;

P is a GRP receptor peptide antagonist of the general formula:

$Xaa_1$-$Xaa_2$-$Xaa_3$-$Xaa_4$-$Xaa_5$-$Xaa_6$-$Xaa_7$-Z wherein:

$Xaa_1$ is not present or is selected from the group consisting of amino acid residues Asn, Thr, Phe, 3-(2-thienyl) alanine (Thi), 4-chlorophenylalanine (Cpa), α-naphthylalanine (α-Nal), β-naphthylalanine (β-Nal), 1,2,3,4-tetrahydronorharman-3-carboxylic acid (Tpi), Tyr, 3-iodo-tyrosine (o-I-Tyr), Trp, pentafluorophenylalanine (5-F-Phe) (all as L- or D-isomers);

$Xaa_2$ is Gln, Asn, His $Xaa_3$ is Trp, 1,2,3,4-tetrahydronorharman-3-carboxylic acid (Tpi)

$Xaa_4$ is Ala, Ser, Val $Xaa_5$ is Val, Ser, Thr $Xaa_6$ is Gly, sarcosine (Sar), D-Ala, p-Ala $Xaa_7$ is His, (3-methyl)histidine (3-Me)His Z is selected from —NHOH, —$NHNH_2$, —NH-alkyl, —$N(alkyl)_2$, or —O-alkyl or

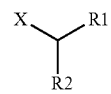

wherein X is NH (amide) or O (ester) and R1 and R2 are the same or different and selected from a proton, a (substituted)alkyl, a (substituted) alkyl ether, an aryl, an aryl ether or an alkyl-, halogen, hydroxyl or hydroxyalkyl substituted aromatic group.

Z is preferably selected from one of the following formulae, wherein X is NH or O:

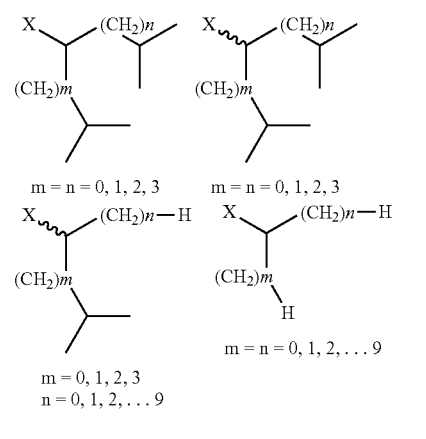

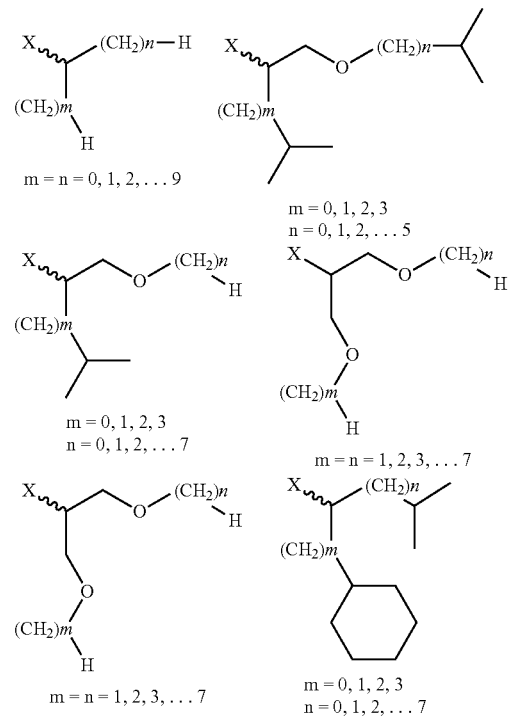

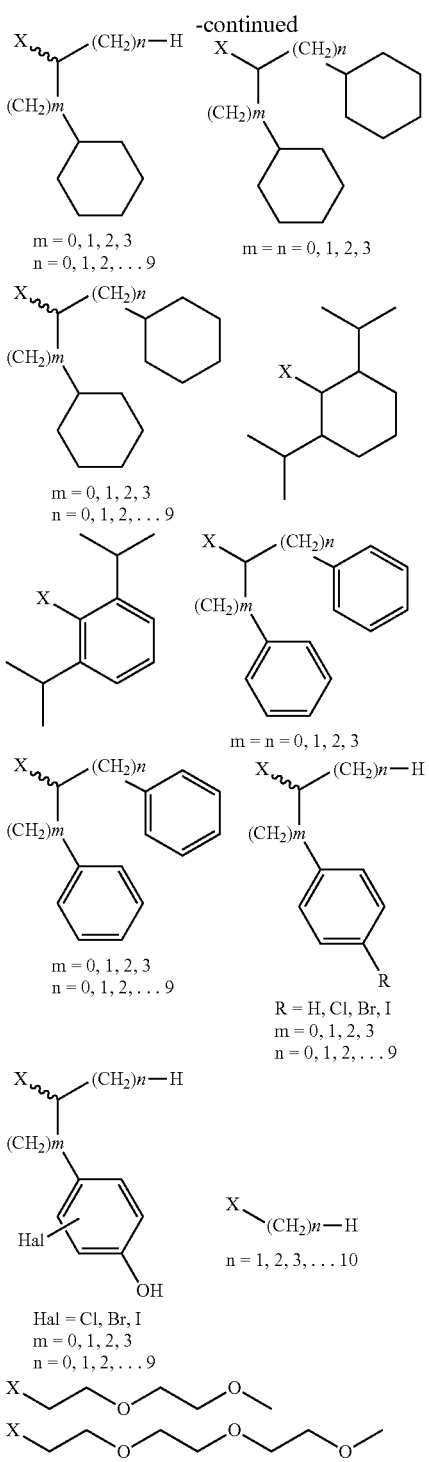

Preferably, R1 is the same as R2.

In the GRPR-antagonists of the invention P is preferably selected from the group consisting of:

(SEQ ID NO: 1)
DPhe-Gln-Trp-Ala-Val-Gly-His- NH—CH[CH₂—CH(CH₃)₂]₂;

(SEQ ID NO: 2)
DPhe-Gln-Trp-Ala-Val-Gly-His- O—CH[CH₂—CH(CH₃)₂]₂;

(SEQ ID NO: 3)
DPhe-Gln-Trp-Ala-Val-Gly-His-
NH—CH(CH₂—CH₂—CH₂—CH₃)₂;

(SEQ ID NO: 4)
DTyr-Gln-Trp-Ala-Val-Gly-His- NH—CH[CH₂—CH(CH₃)₂]₂.

The radionuclide, a metal M or a halogen, is suitable for diagnostic or therapeutic use, in particular for imaging or radionuclide therapy and preferably selected from the group consisting of $^{111}$In, $^{133m}$In, $^{99m}$Tc, $^{94m}$Tc, $^{67}$Ga, $^{66}$Ga, $^{68}$Ga, $^{52}$Fe, $^{69}$Er, $^{72}$As, 97Ru, $^{203}$Pb, $^{62}$Cu, $^{64}$Cu, $^{67}$Cu, $^{186}$Re, $^{188}$Re, $^{86}$Y, $^{90}$Y, $^{51}$Cr, $^{52m}$Mn, $^{157}$Gd, $^{177}$Lu, $^{161}$Tb, $^{169}$Yb, $^{175}$Yb, $^{105}$Rh, $^{166}$Dy, $^{166}$Ho, $^{153}$Sm, $^{149}$Pm, $^{151}$PM, $^{172}$Tm, $^{121}$Sn, $^{177m}$Sn, $^{213}$Bi, $^{142}$Pr, $^{143}$Pr, $^{198}_{Au,}$ $^{199}$Au, $^{123}$I, $^{124}$I, $^{125}$I, $^{18}$F a.o.

The metal chelator C is preferably a metal chelator for di- and trivalent metals, and is in particular a DTPA-, NOTA-, DOTA-, or TETA-based chelator or a mono- or bifunctional derivative thereof.

Preferably, the metal chelator C is selected from the group consisting of:

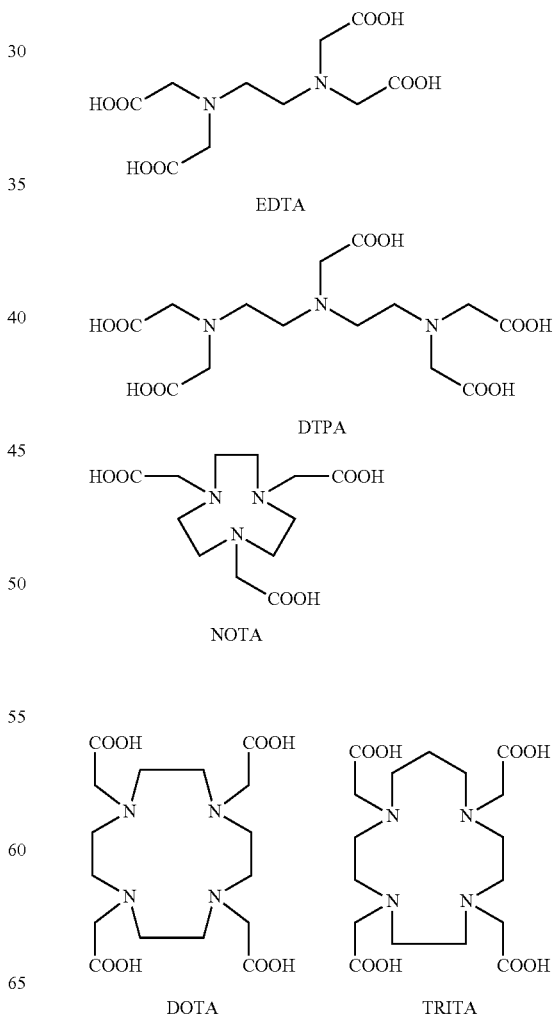

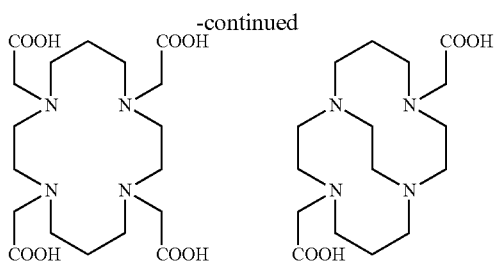

TETA / CB-TE2A

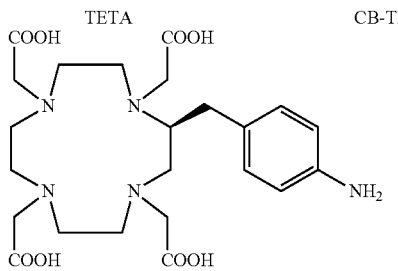

bifunctional DOTA

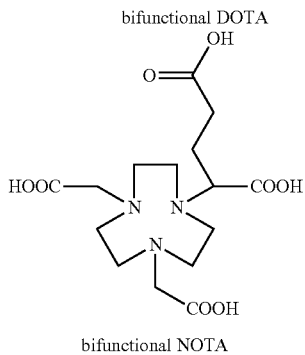

bifunctional NOTA

When the metal chelator C is a metal chelator for technetium or rhenium, it is preferably selected from acyclic tetraamine-, cyclam-, PnAO-, or tetradentate chelators containing $P_2S_2$-, $N_2S_2$- and $N_3S$-donor atom sets and mono- and bifunctional derivatives thereof, or HYNIC/co-ligand-based chelators, or bi- and tridentate chelators forming organometallic complexes via the tricarbonyl technology.

Suitable examples of C are:

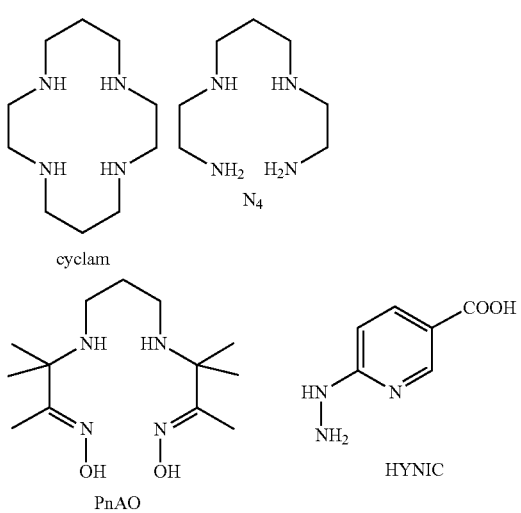

cyclam

PnAO

HYNIC

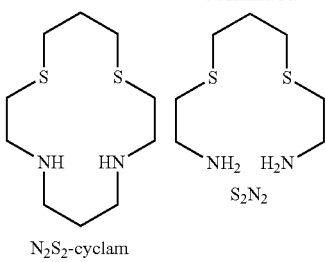

$N_2S_2$-cyclam / $S_2N_2$

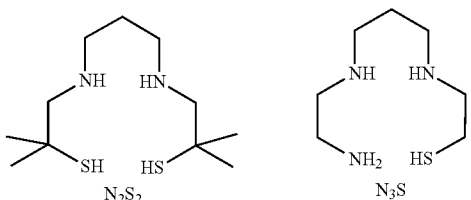

$N_2S_2$ / $N_3S$

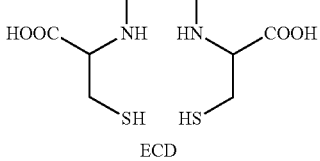

ECD

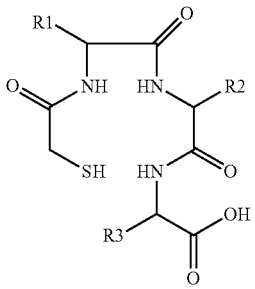

$MAG_3$ (R1 = R2 = R3 = H)

-Xaa-Cys-Xaa-Cys-Xaa-

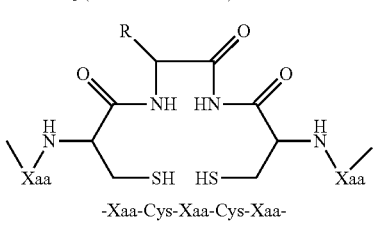

$P_2S_2$ or: M = Tc, Re

The spacer S is linked between P and C by covalent bonds and may be selected to provide a means for using a radiohalogen, such as (radio)iodination. The spacer is preferably selected from the group consisting of:

a) aryl containing residues of the formulae:

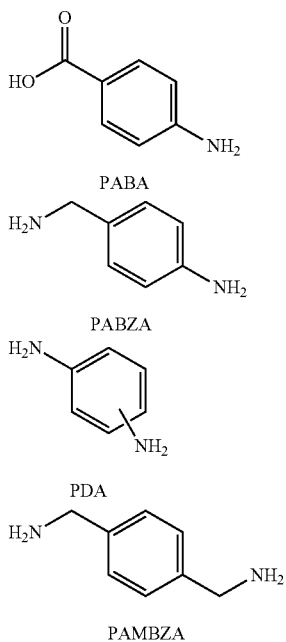

wherein PABA is p-aminobenzoic acid, PABZA is p-aminobenzylamine, PDA is phenylenediamine and PAMBZA is p-(aminomethyl)benzylamine;

b) dicarboxylic acids, ω-aminocarboxylic acids, α,ω-diaminocarboxylic acids or diamines of the formulae:

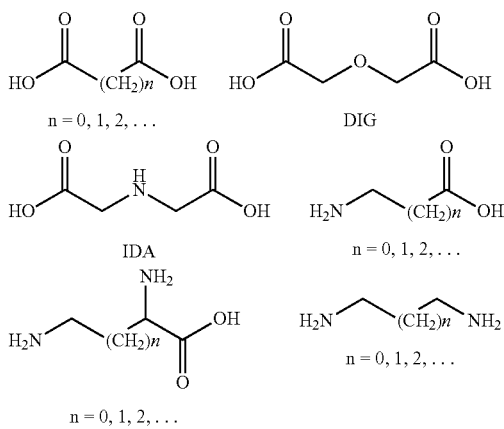

wherein DIG is diglycolic acid and IDA is iminodiacetic acid;

c) PEG spacers of various chain lengths, in particular PEG spacers selected from the formulae:

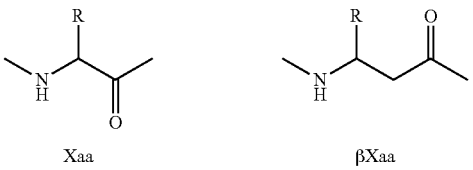

$n = 1, 2, 3, \ldots$ until 36
$m = 0, 1, 2, 3, 4, 5$ d) α- and β-amino acids, single or in homologous chains of various chain lengths or heterologous chains of various chain lengths, in particular:

Xaa   βXaa

GRP(1-18), GRP(14-18), GRP(13-18), BBN(1-5), or [Tyr$^4$]BBN(1-5); or e) combinations of a, b and c.

GRPR-antagonists of the invention are preferably selected from the group consisting of compounds of the formulae:

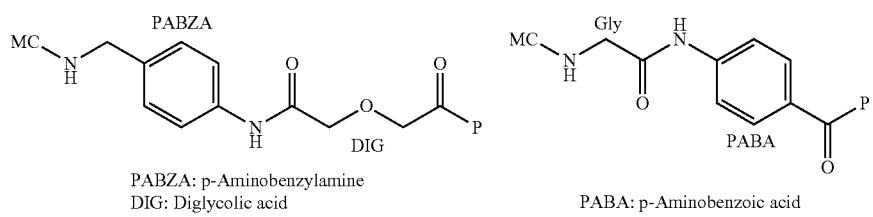

PABZA: p-Aminobenzylamine
DIG: Diglycolic acid

PABA: p-Aminobenzoic acid

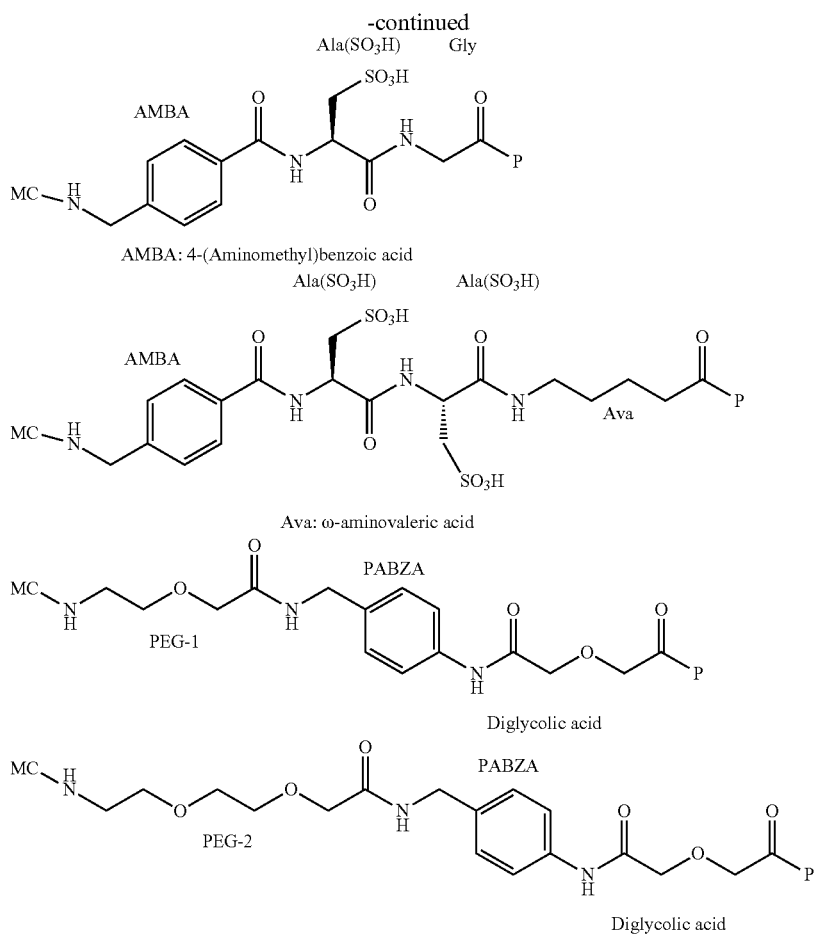

wherein MC and P are as defined above.

It is understood that specific chemical structures disclosed herein are illustrative examples of various embodiments of the invention and that GRPR-antagonists of the general formula: MC-S-P are not limited to the structures of examples provided.

The invention further relates to a therapeutic composition, comprising a GRPR-antagonist as claimed and a therapeutically acceptable excipient.

The invention also relates to the GRPR-antagonists as claimed for use as a medicament. The medicament is preferably a diagnostic or therapeutic agent for diagnosing or treating primary and/or metastatic GRPR+ cancers, such as prostate cancer, breast cancer, small cell lung cancer, colon carcinoma, gastrointestinal stromal tumors, gastrinoma, renal cell carcinomas, gastroenteropancreatic neuroendocrine tumors, oesophageal squamous cell tumors, neuroblastomas, head and neck squamous cell carcinomas, to name some of the few, as well as in vasculature of ovarian, endometrial and pancreatic tumors.

The invention will be further illustrated in the Examples that follows and which are not intended to limit the invention in any way.

EXAMPLE

Introduction

Compounds of the invention were made and tested as described below. The following disclosed embodiments are merely representative of the invention which may be embodied in various forms. Thus, specific structural, functional, and procedural details disclosed in the following examples are not to be interpreted as limiting.

Materials and Methods

Radiolabeling and QC

Labeling with $^{111}$In

Indium (In-111) chloride in 50 mM HCl was purchased from Mallinckrodt Medical B.V., Petten, The Netherlands, at an activity concentration of 10-20 mCi/mL. In general, DOTA-peptide conjugates of the present invention were radiolabeled with Indium-111 at specific activities of 0.1-0.2 mCi In-111/nmol DOTA-peptide conjugate. Briefly, 3-15 nmol of DOTA-peptide conjugate dissolved in water was mixed with 2.5-12.5 μL of 1.0 M pH 4.6 sodium acetate buffer, 1-5 μL of 0.1 M sodium ascorbate in water and 30-150 μL of $^{111}$InCl$_3$ (0.3-3.0 mCi). The radiolabeling reaction mixture was incubated in a boiling water bath for 20 to 30 min. For quality control a 2 μL aliquot of the radiolabeling solution was quenched with 28 μL of an acetate buffered solution of Na$_2$-EDTA (5 mM, pH 4.6). After a successful radiolabeling (more than 95% peptide-bound radioactivity) Na$_2$-EDTA (0.1 M, pH 4.6) was added to the radiolabeling solution to a final concentration of 1 mM.

Labeling with $^{67}$Ga

Gallium (Ga-67) chloride was obtained either in dilute HCl at an activity concentration of 498-743 mCi/mL from Nordion, Wesbrook Mall, Vancouver, Canada or at an activity concentration of 80 mCi/mL from Mallinckrodt Medical B.V., Petten, The Netherlands.

In general, DOTA-peptide conjugates of the present invention were radiolabeled with Gallium-67 at specific activities of 0.1-0.2 mCi Ga-67/nmol DOTA-peptide conjugate. Briefly, 3-15 nmol of DOTA-peptide conjugate dissolved in water was mixed with 50-125 µL of 1.0 M pH 4.0 sodium acetate buffer and 5-15 µL of $^{67}$GaCl$_3$ (0.5-3.0 mCi. The radiolabeling reaction mixture was incubated in a boiling water bath for 30 min. For HPLC quality control a 2 µL aliquot of the radiolabeling solution was quenched with 28 µL of an acetate buffered solution of Na$_2$-EDTA (5 mM, pH 4.0). After a successful labeling (more than 95% peptide-bound radioactivity) Na$_2$-EDTA (0.1 M, pH 4.0) was added to the radiolabeling solution to a final concentration of 1 mM.

Labeling with $^{177}$Lu

Lutetium (Lu-177) chloride in 50 mM HCl was purchased from IDB Radiopharmacy, The Netherlands, at an activity concentration of 100 mCi/mL.

In general, DOTA-peptide conjugates of the present invention were radiolabeled with Lutetium-177 to a specific activity of up to 0.5 mCi Lu-177/nmol DOTA-peptide conjugate. Briefly, 3-15 nmol of DOTA-peptide conjugate dissolved in water was mixed with 4-16 µL of 1.0 M pH 4.6 sodium acetate buffer and 15-75 µL of $^{67}$GaCl$_3$ (1.5-7.5 mCi). Radiolysis was minimized by the addition of 5 µl of gentisic acid (80 mM) dissolved in 0.2 M sodium ascorbate. The reaction mixture was incubated in a boiling water bath for 30 min. For HPLC quality control a 2 µL aliquot of the radiolabeling solution was quenched with 28 µL of an acetate buffered solution of Na$_2$-EDTA (5 mM, pH 4.6). After a successful radiolabeling (more than 95% peptide-bound radioactivity) Na$_2$-EDTA (0.1 M, pH 4.6) was added to the radiolabeling solution to a final concentration of 1 mM.

Labeling with $^{99m}$Tc

Tetraamine-coupled peptides were dissolved in 50 mM acetic acid/EtOH 8/2 v/v to a final 1 mM peptide concentration. Each bulk solution was distributed in 50 µL aliquots in Eppendorf tubes and stored at −20° C. Labeling was conducted in an Eppendorf vial, wherein the following solutions were consecutively added: i) 0.5 M phosphate buffer pH 11.5 (50 µL), ii) 0.1 M sodium citrate (5 µL, iii) [$^{99m}$Tc]NaTcO$_4$ generator eluate (415 mL, 10-20 mCi), iv) peptide conjugate stock solution (15 µL, 15 nmol) and v) freshly made SnCl$_2$ solution in EtOH (30 µg, 15 µL). After reaction for 30 min at ambient temperature, the pH was brought to ~7 by adding 1 M HCl (10 µL).

Quality Control

HPLC analyses were conducted on a Waters Chromatograph (Waters, Vienna, Austria) efficient with a 600 solvent delivery system; the chromatograph was coupled to twin detection instrumentation, comprising a photodiode array UV detector (either Waters model 996 or model 2998) and a Gabi gamma detector from Raytest (RSM Analytische Instrumente GmbH, Germany). Data processing and chromatography were controlled via the Millennium or Empower 2 Software (Waters, USA). A XBridge Shield RP18 column (5 µm, 4.6×150 mm, Waters, Ireland) coupled to the respective 2-cm guard column was eluted at 1 ml/min flow rate with a linear gradient system starting from 10% B and advancing to 70% B within 60 min, with solvent A=0.1% aqueous trifluoroacetic acid and solvent B=acetonitrile.

Metabolic Study in Mice

Radioligand Injection and Blood Collection

A bolus containing the radioligand in normal saline (100-150 µL, ≈3 nmol, 200-500 µCi) was injected in the tail vein of Swiss albino mice. Animals were kept for 5 min in a cage with access to water and were then euthanized promptly by cardiac puncture while under a mild ether anesthesia. Blood (500-900 µL) was collected from the heart with a syringe and transferred in a pre-chilled Eppendorf tube on ice.

Plasma Separation and Sample Preparation

Blood was centrifuged to remove blood cells (10 min, 2000 g/4° C.). The plasma was collected, mixed with acetonitrile (MeCN) in a 1/1 v/v ratio and centrifuged again (10 min, 15000 g/4° C.). Supernatants were concentrated to a small volume (gentle N$_2$-flux at 40° C.), diluted with saline 400 µL) and filtered through a Millex GV filter (0.22 µm).

HPLC Analysis for Radiometabolite Detection

Aliquots of plasma samples (prepared as described above) were loaded on a Symmetry Shield RPM column which was eluted at a flow rate of 1.0 mL/min with the following gradient: 100% A to 90% A in 10 min and from 90% A to 60% for the next 60 min (A=0.1% aqueous TFA (v/v) and B=MeCN). Elution of radiocomponents was monitored by a gamma detector. For $^{99m}$Tc-radiopeptides, ITLC-SG analysis was performed in parallel using acetone as the eluent to detect traces of TcO$_4^-$ release (TcO$_4^-$ Rf=1.0).

Studies in GRPR$^+$-Tumor Bearing Mice

Tumor Induction

A ≈X150 µL bolus containing a suspension of 1.5×10$^7$ freshly harvested human PC-3 cells in normal saline was subcutaneously injected in the flanks of female SCID mice. The animals were kept under aseptic conditions and 2-3 weeks later developed well-palpable tumors at the inoculation site (80-150 mg).

Biodistribution and Calculation of Results

On the day of the experiment, the selected radiopeptide was injected in the tail vein of tumor-bearing mice as a 100 µL bolus (1-2 µCi, 10 pmol total peptide; in saline/EtOH 9/1 v/v). Animals were sacrificed in groups of four under a mild ether anesthesia by cardiac puncture at predetermined time points pi (postinjection). Additional sets of three to four animals were co-injected with excess [Tyr$^4$]BBN (>40 nmol) along with test radiopeptide and were sacrificed at 4 h pi (blocked animals). Samples of blood and tissues of interest were immediately collected, weighed and measured for radioactivity in a γ-counter. Stomach and intestines were not emptied of their contents, but measured as collected. Biodistribution data were calculated as percent injected dose per gram tissue (% ID/g) using the Microsoft Excel program with the aid of suitable standards of the injected dose.

Results

The results of the various illustrative tests are described herebelow by referring to the corresponding figure. Specific structural, functional, and procedural details disclosed in the following results are not to be interpreted as limiting.

FIG. 1A: Biodistribution of [$^{111}$In]NeoBOMB-1 ($^{111}$In-DOTA-(p-aminobenzylamine-diglycolic acid)-[D-Phe$^6$,His-NHCH[(CH$_2$CH(CH$_3$)$_2$]$_2$$^{12}$,des-Leu$^{13}$,des-Met$^{14}$]BBN(6-14)) in female SCID mice bearing PC-3 tumors (hGRPR$^+$) at 4 h and 24 h pi. Bars represent average uptake as % injected dose per gram (% ID/g) of at least 4 animals with standard deviation; an additional group of animals received excess [Tyr$^4$]BBN (100 μg) for in vivo receptor blockade at 4 h pi. Bl=blood, Li=liver, He=heart, Ki=kidneys, St=stomach, In=intestines, Sp=spleen, Mu=muscle, Lu=lungs, Pa=pancreas, Fe=femur and Tu=PC-3 tumor. High uptake and retention is observed in the experimental tumor with 28.6±6.0% ID/g at 4 h and 25.9±6.6% ID/g at 24 h. A high percentage of this uptake could be significantly reduced by co-injection of excess of a native bombesin analog.

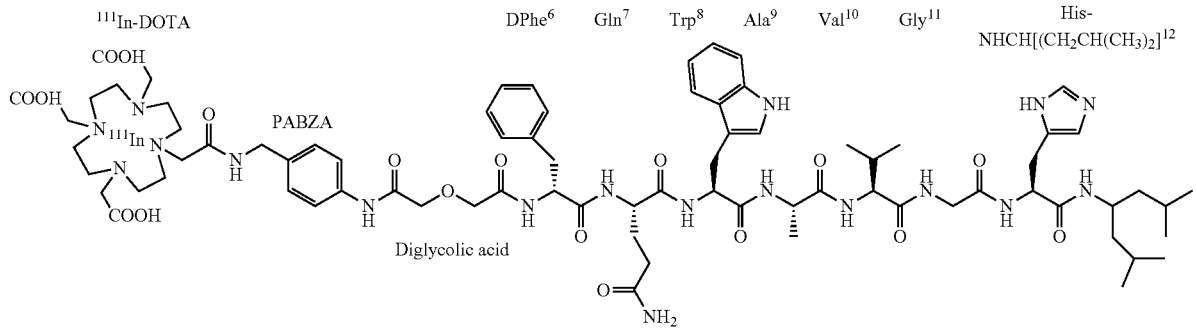

Figure 1B:
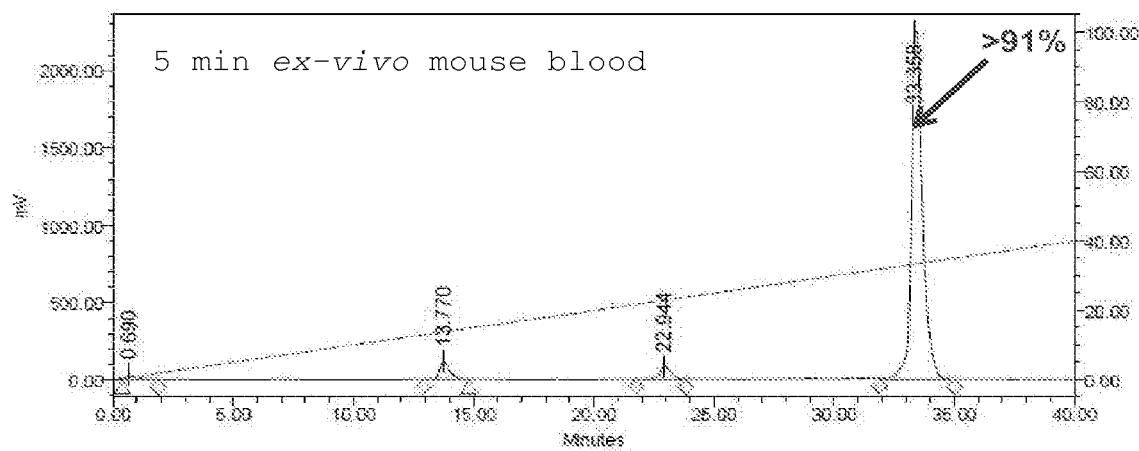
FIG. 1B. Shows a radiochromatogram of ex-vivo mouse blood 5 min after injection of [$^{111}$In]NeoBOMB-1.

FIG. 1B: Radiochromatogram of ex-vivo mouse blood 5 min after injection of [$^{111}$In]NeoBOMB-1. The percentage of parent peptide remaining intact is >91%.

Figure 1C:
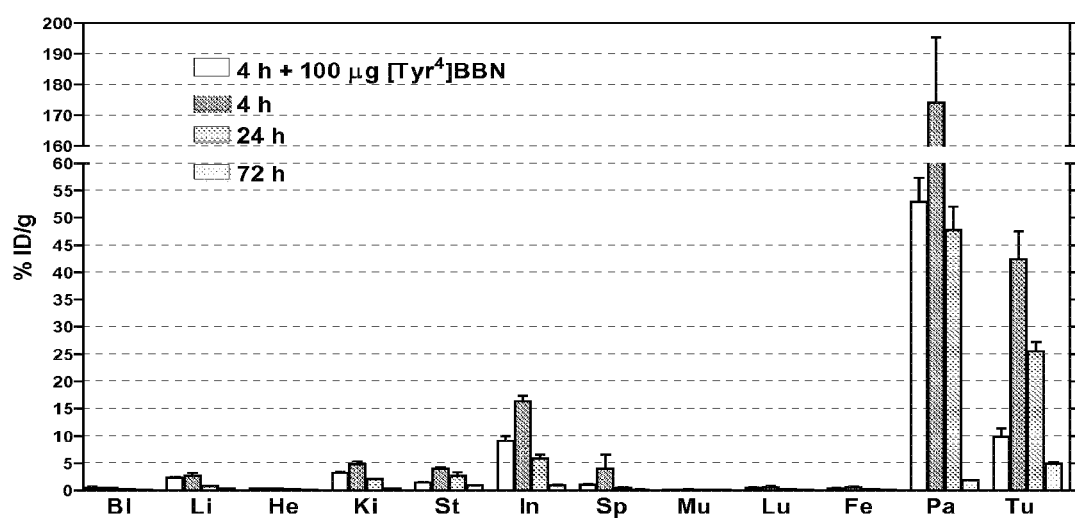
FIG. 1C. Shows the biodistribution of [$^{177}$Lu]NeoBOMB-1 ($^{177}$Lu-DOTA-(p-aminobenzylamine-diglycolic acid)-[D-Phe$^6$,His-NHCH[(CH$_2$CH(CH$_3$)$_2$]$_2$$^{12}$,des-Leu$^{13}$,des-Met$^{14}$]BBN(6-14)) in female SCID mice bearing PC-3 tumors (hGRPR$^+$).

FIG. 1C: Biodistribution of [$^{177}$Lu]NeoBOMB-1 ($^{177}$Lu-DOTA-(p-aminobenzylamine-diglycolic acid)-[D-Phe$^6$,His-NHCH[(CH$_2$CH(CH$_3$)$_2$]$_2$$^{12}$,des-Leu$^{13}$,des-Met$^{14}$]BBN(6-14)) in female SCID mice bearing PC-3 tumors (hGRPR$^+$) at 4, 24 and 72 h pi. Bars represent average uptake as % injected dose per gram (% ID/g) of at least 4 animals with standard deviation; an additional group of animals received excess [Tyr$^4$]BBN (100 μg) for in vivo receptor blockade at 4 h pi. Bl=blood, Li=liver, He=heart, Ki=kidneys, St=stomach, In=intestines, Sp=spleen, Mu=muscle, Lu=lungs, Pa=pancreas, Fe=femur and Tu=PC-3 tumor. Pancreatic uptake declines more rapidly with time than tumor uptake resulting in increasingly higher tumor-to-pancreas ratios, especially at 72 h pi.

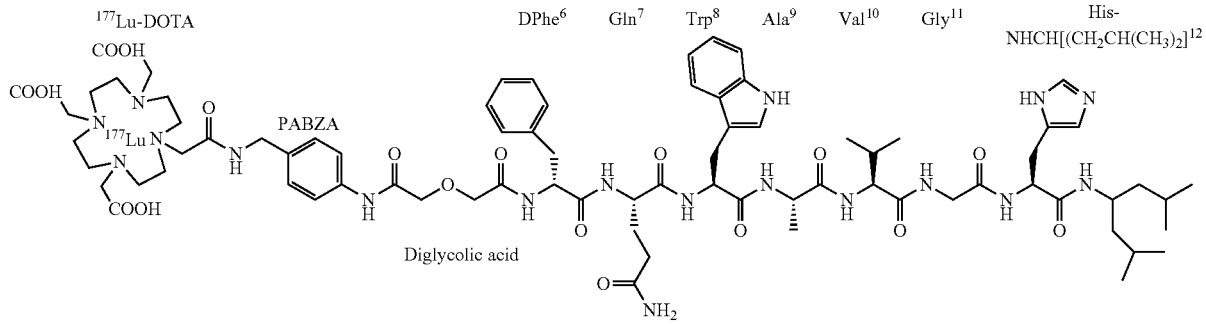

Figure 1D:
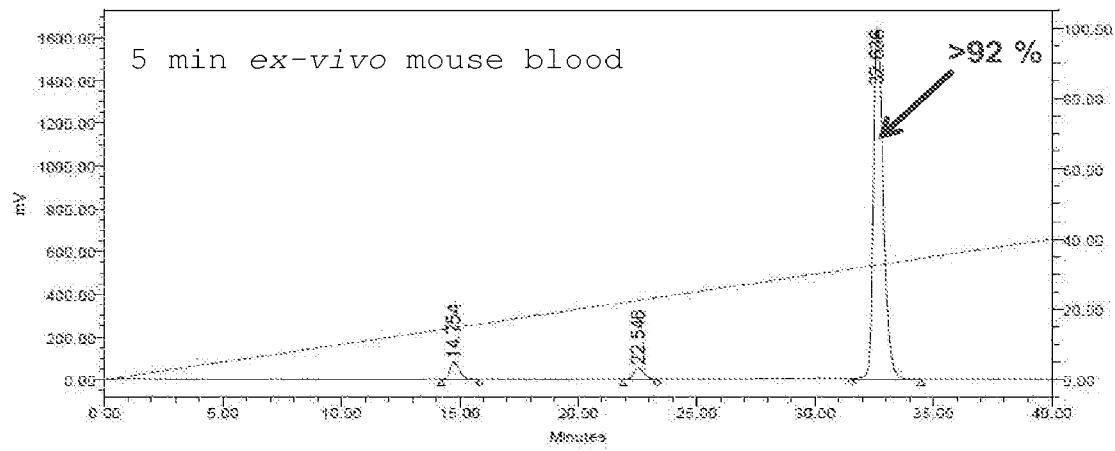
FIG. 1D. Shows a radiochromatogram of ex-vivo mouse blood 5 min after injection of [$^{177}$Lu]NeoBOMB-1.

FIG. 1D: Radiochromatogram of ex-vivo mouse blood 5 min after injection of [$^{177}$Lu]NeoBOMB-1, shows that >92% parent peptide remains intact.

Figure 1E:
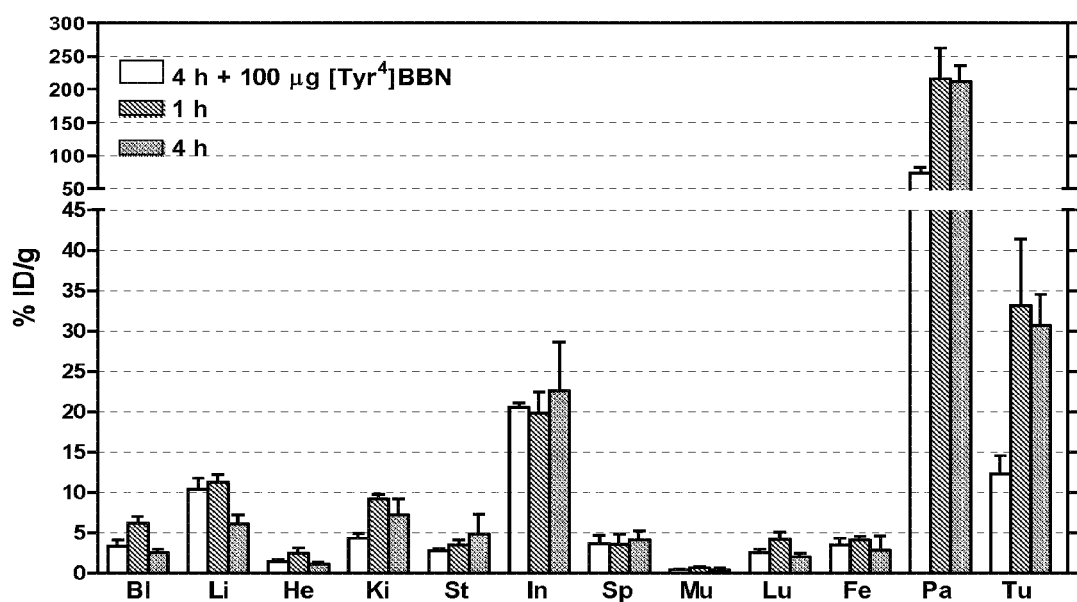
FIG. 1E. Shows the biodistribution of [$^{67}$Ga]NeoBOMB-1 ($^{67}$Ga-DOTA-(p-aminobenzylamine-diglycolic acid)-[D-Phe$^6$,His-NHCH[(CH$_2$CH(CH$_3$)$_2$]$_2$$^{12}$,des-Leu$^{13}$,des-Met$^{14}$]BBN(6-14)) in female SCID mice bearing PC-3 tumors (hGRPR$^+$).

FIG. 1E: Biodistribution of [$^{67}$Ga]NeoBOMB-1 ($^{67}$Ga-DOTA-(p-aminobenzylamine-diglycolic acid)-[D-Phe$^6$,His-NHCH[(CH$_2$CH(CH$_3$)$_2$]$_2$$^{12}$,des-Leu$^{13}$,des-Met$^{14}$]BBN(6-14)) in female SCID mice bearing PC-3 tumors (hGRPR$^+$) at 1 h and 4 h pi. Bars represent average uptake as % injected dose per gram (% ID/g) of at least 4 animals with standard deviation; an additional group of animals received excess [Tyr$^4$]BBN (100 µg) for in vivo receptor blockade at 4 h pi. Bl=blood, Li=liver, He=heart, Ki=kidneys, St=stomach, In=intestines, Sp=spleen, Mu=muscle, Lu=lungs, Pa=pancreas, Fe=femur and Tu=PC-3 tumor. High tumor values (>30% ID/g) are achieved by the radiotracer at 1 and 4 h pi.

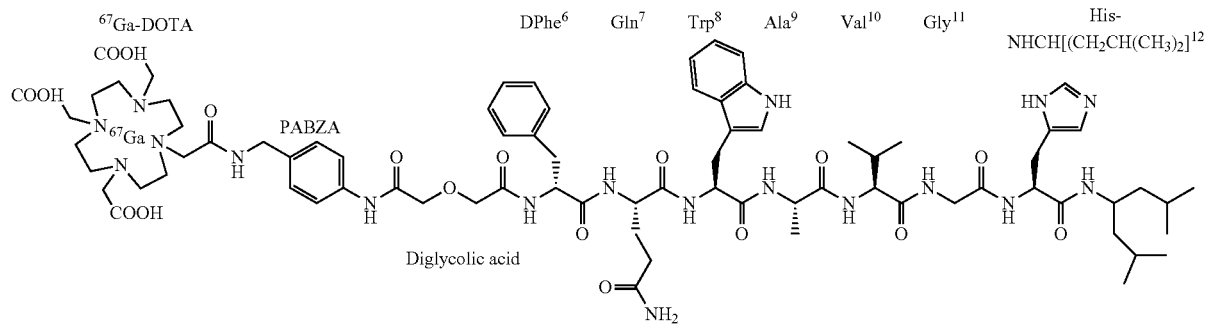

Figure 1F:
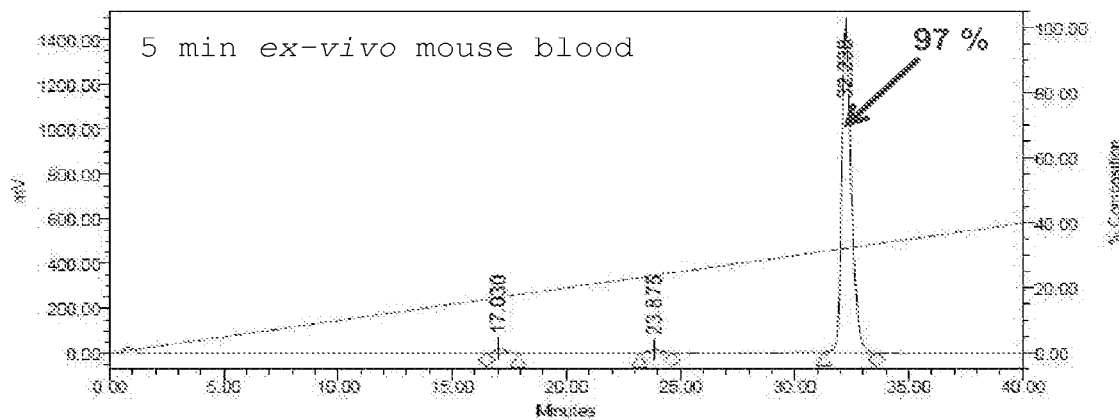
FIG. 1F. Shows a radiochromatogram of ex-vivo mouse blood 5 min after injection of [$^{67}$Ga]NeoBOMB-1.

FIG. 1F: Radiochromatogram of ex-vivo mouse blood 5 min after injection of [$^{67}$Ga]NeoBOMB-1, shows that >97% parent peptide remains intact.

Figure 2A:
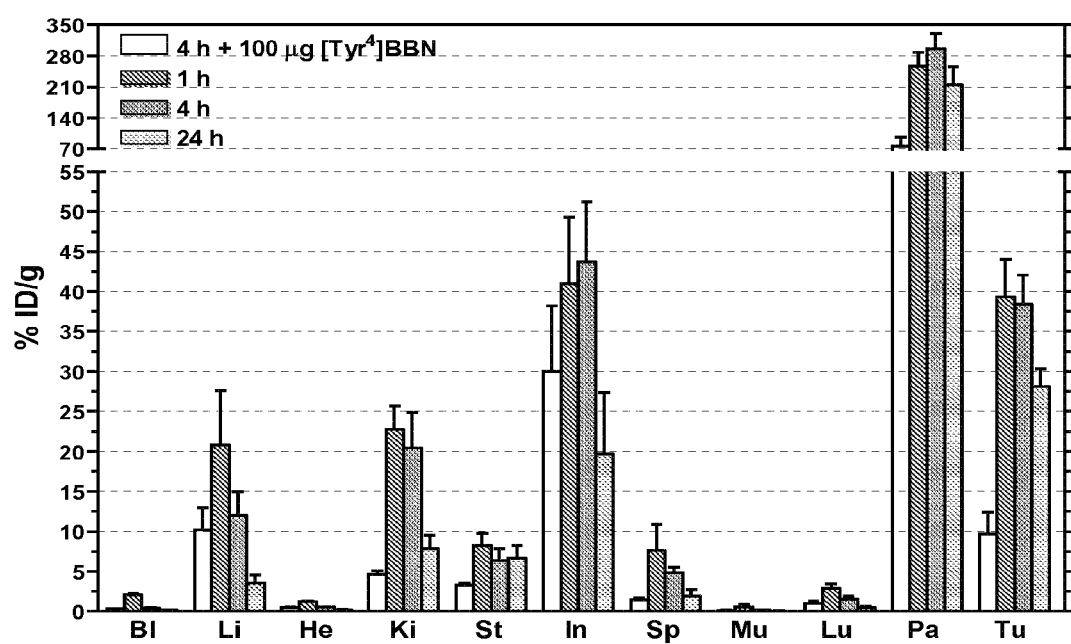
FIG. 2A. Shows the biodistribution of [$^{99m}$Tc]NeoBOMB-2 ($^{99m}$Tc-N$_4$-(p-aminobenzylamine-diglycolic acid)-[D-Phe$^6$,His-NHCH[(CH$_2$CH(CH$_3$)$_2$]$_2$$^{12}$,des-Leu$^{13}$,des-Met$^{14}$]BBN(6-14)) in female SCID mice bearing PC-3 tumors (hGRPR$^+$).

FIG. 2A: Biodistribution of [$^{99m}$Tc]NeoBOMB-2 ($^{99m}$Tc—N$_4$-(p-aminobenzylamine-diglycolic acid)-[D-Phe$^6$,His-NHCH[(CH$_2$-CH(CH$_3$)$_2$]$_2$$^{12}$,des-Leu$^{13}$,des-Met$^{14}$]BBN(6-14)) in female SCID mice bearing PC-3 tumors (hGRPR$^+$) at 1 h, 4 h and 24 h pi. Bars represent average uptake as % injected dose per gram (% ID/g) of at least 4 animals with standard deviation; an additional group of animals received excess [Tyr$^4$]BBN (100 µg) for in vivo receptor blockade at 4 h pi. Bl=blood, Li=liver, He=heart, Ki=kidneys, St=stomach, In=intestines, Sp=spleen, Mu=muscle, Lu=lungs, Pa=pancreas and Tu=PC-3 tumor. High tumor values (~30% ID/g) are achieved by the radiotracer at 1 and 4 h pi, which remain exceptionally high (>25% ID/g) at 24 h pi.

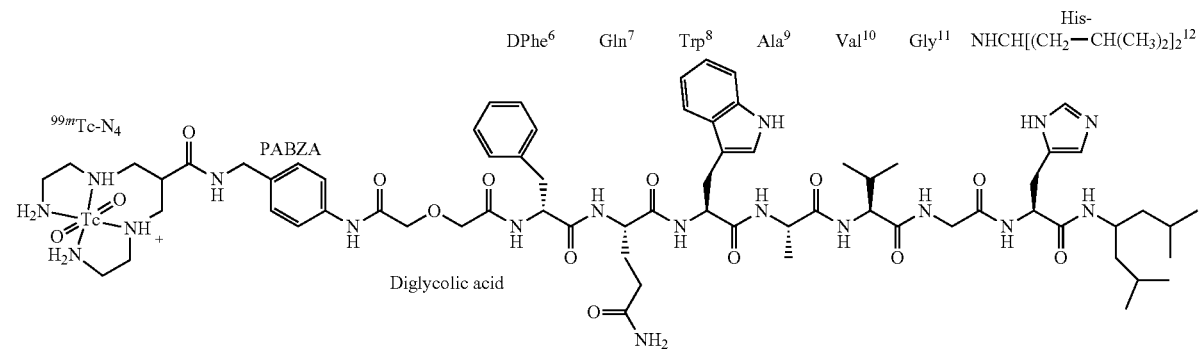

Figure 2B:
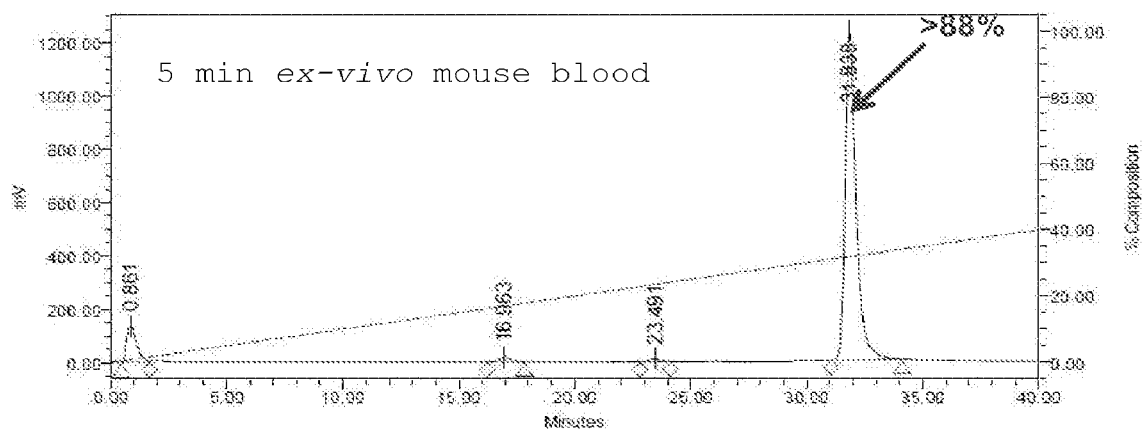
FIG. 2B. Shows a radiochromatogram of ex-vivo mouse blood 5 min after injection of [$^{99m}$Tc]NeoBOMB-2.

FIG. 2B: Radiochromatogram of ex-vivo mouse blood 5 min after injection of [$^{99m}$Tc]NeoBOMB-2 shows that >88% parent peptide remains intact.

What is claimed is:

1. A radiolabeled GRPR-antagonist of the formula MC-S-P wherein:

M is a radiometal and C is a metal chelator that binds M,

S is a spacer covalently linked between C and P of formula:

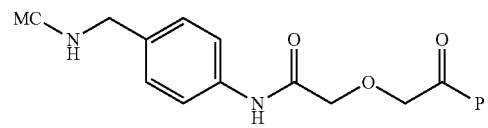

wherein S is covalently attached to the N-terminus of P; and P is

DPhe-Gln-Trp-Ala-Val-Gly-His-NH-CH[CH$_2$-CH(CH$_3$)$_2$]$_2$ (SEQ ID NO: 1);

wherein M is $^{68}$Ga.

2. A radiolabeled GRPR-antagonist of the following formula:

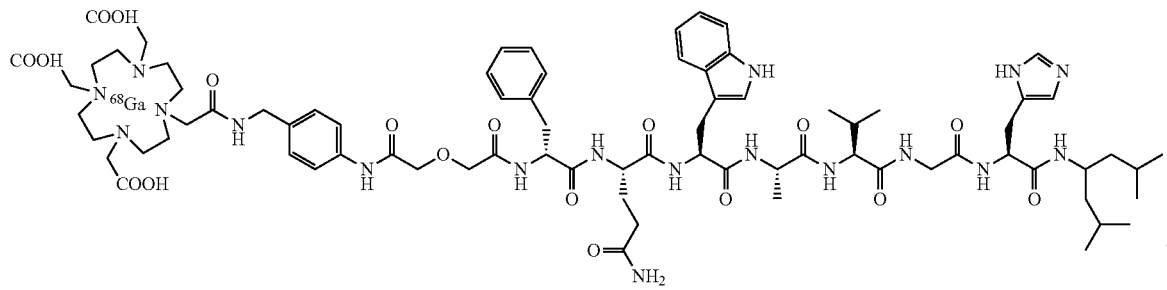

3. A method of detecting a primary and/or metastatic GRPR-positive cancer in a human subject comprising administering the radiolabeled GRPR-antagonists as claimed in claim 1 to the human subject, imaging the subject, and detecting the radiolabeled GRPR-antagonist bound to GRPR wherein the cancer is selected from prostate cancer, breast cancer, small cell lung cancer, colon cancer, gastrointestinal stromal tumors, gastrinoma, renal cell carcinomas, gastroenteropancreatic neuroendocrine tumors, oesophageal squamous cell tumors, neuroblastomas, head and neck squamous cell carcinomas, ovarian cancer, endometrial cancer, and pancreatic cancer.

4. A method of detecting a primary and/or metastatic GRPR-positive cancer in a human subject comprising administering the radiolabeled GRPR-antagonists as claimed in claim 2 to the human subject, imaging the subject, and detecting the radiolabeled GRPR-antagonist bound to GRPR wherein the cancer is selected from prostate cancer, breast cancer, small cell lung cancer, colon cancer, gastrointestinal stromal tumors, gastrinoma, renal cell carcinomas, gastroenteropancreatic neuroendocrine tumors, oesophageal squamous cell tumors, neuroblastomas, head and neck squamous cell carcinomas, ovarian cancer, endometrial cancer, and pancreatic cancer.

5. The method of claim 3 wherein the imaging of the radiolabeled GRPR-antagonist bound to GRPR is performed with a PET or a hybrid PET/CT or PET/MRI system.

6. The method of claim 4 wherein the imaging of the radiolabeled GRPR-antagonist bound to GRPR is performed with a PET or a hybrid PET/CT or PET/MRI system.

7. A pharmaceutical composition comprising a radiolabeled GRPR-antagonist as claimed in claim 1 and a pharmaceutically acceptable excipient.

8. A pharmaceutical composition comprising a radiolabeled GRPR-antagonist as claimed in claim 2 and a pharmaceutically acceptable excipient.

9. The radiolabeled GRPR-antagonist of claim 1, wherein the metal chelator C is DOTA.

* * * * *